United States Patent [19]
Colsky

[11] Patent Number: 5,242,401
[45] Date of Patent: Sep. 7, 1993

[54] DISPOSABLE NEEDLE HEAD ASSEMBLY

[76] Inventor: Andrew E. Colsky, 49 Merrick Way, Suite 208, Coral Gables, Fla. 33134

[21] Appl. No.: 958,811

[22] Filed: Oct. 9, 1992

[51] Int. Cl.⁵ .............................................. A61M 5/00
[52] U.S. Cl. .................................... 604/110; 604/198
[58] Field of Search ............... 604/110, 198, 192, 187, 604/240–243, 263, 905

[56] References Cited

U.S. PATENT DOCUMENTS

| | | | |
|---|---|---|---|
| 4,813,940 | 3/1989 | Parry | 604/198 |
| 4,894,055 | 1/1990 | Sudnak | 604/110 X |
| 4,961,730 | 10/1990 | Poncy | 604/198 |
| 5,024,660 | 6/1991 | McNaughton | 604/110 |

*Primary Examiner*—John D. Yasko
*Attorney, Agent, or Firm*—Malloy & Malloy

[57] ABSTRACT

A disposable needle head assembly including a needle portion having a protruding hypodermic needle and a hub portion adapted to be secured to a standard syringe body, and a cover portion, the cover portion being slidingly disposed over the needle portion and including an internally extending nub which travels along a recessed track formed in an exterior of the hub of the needle portion, thereby guiding the axial movement of the cover portion about the needle portion and causing the cover portion to be accordingly positioned in a needle exposing position during use, and an extended needle, containing position in to which the cover portion is engaged automatically after use of the hypodermic needle.

15 Claims, 2 Drawing Sheets

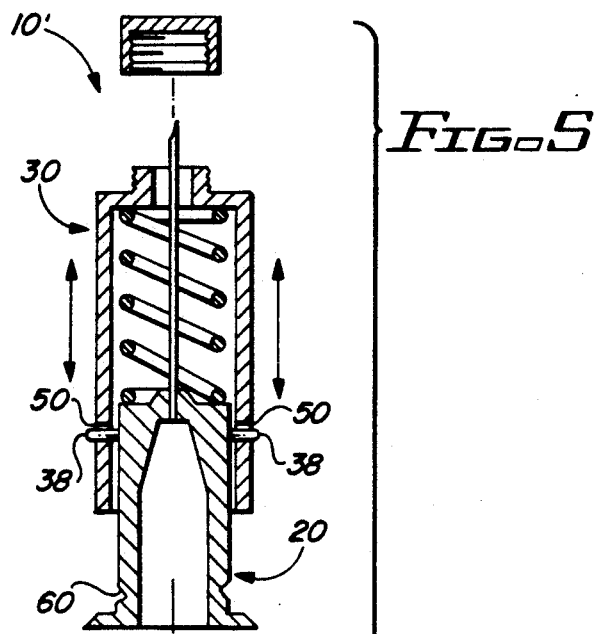
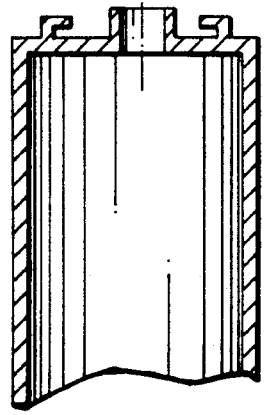
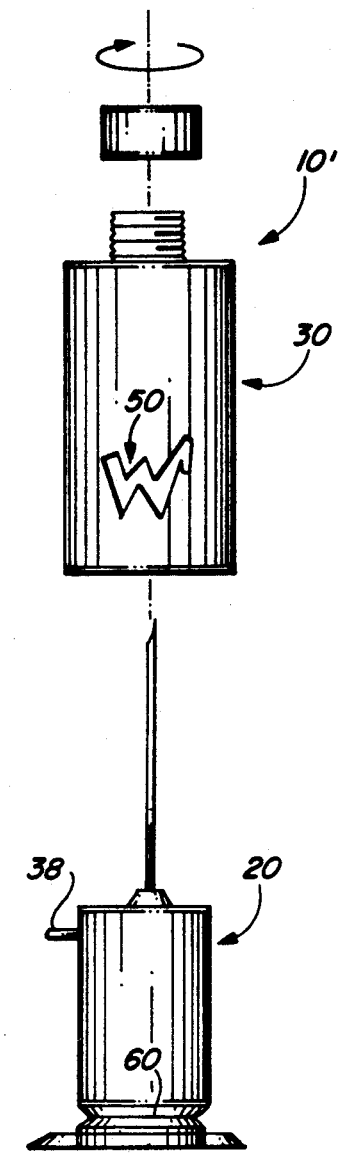
Fig. 5
Fig. 6

DISPOSABLE NEEDLE HEAD ASSEMBLY

BACKGROUND OF THE INVENTION

1. Field of the Invention

The present invention relates to a disposable needle head assembly to be used with a standard syringe body, the needle head assembly being especially adapted to contain and shield a hypodermic needle after use, thereby preventing accidental injury as a result of the hypodermic needle and insuring automatic protection after use of the hypodermic needle.

2. Description of the Related Art

With the increase in the number and severity of numerous contagious, and potentially deadly diseases, such as HIV, and the more informed nature of our society with regard to how these diseases are transmitted, particular attention has been given to the safety requirements associated with the use of hypodermic needles. These needles, after use on sick patients, become contaminated and pose a significant threat to medical attendants, as well as any other individual who may come in contact with a used syringe in the trash or an improperly discarded location. As a result of this pressing need, there have recently been numerous patented inventions directed towards providing a safety shield for a hypodermic needle. Of the protective covers which utilize springs and/or slot arrangements in their design, a majority, such as those recited in Bayless, U.S. Pat. No. 4,863,434, Bayless, U.S. Pat. No. 4,850,977, Burns, et al., U.S. Pat. No. 4,966,592, and Morgan, U.S. Pat. No. 4,923,447, incorporate a protective assembly as part of an entire syringe assembly. Further, they require manual operation of the protective device, which will not protect against carelessness and will not immediately cover the needle, but will rather necessitate that an individual activate the protective covering of a potentially contaminated needle. In addition to being manually effectuated, common medical practice utilizes solely a disposable syringe tip, enabling the syringe body to be reused, thereby making protective coverings which are formed as part of an entire syringe to be non-effective. As a result of the common use of disposable syringe tips, rather than an entire disposable syringe, protective coverings such as those disclosed in Vaillancourt, U.S. Pat. No. 4,725,267 and Perry, U.S. Pat. No. 4,813,940 have incorporated spring activated protective assemblies as part of the syringe tip. Of these references, only Perry does not require manual extending of the protective covering after the needle has been used. The 14 reference to Perry, however, requires initial manual positioning 15 and is adapted to be fitted on a needle after medication to be 16 injected has been drawn into the needle. Accordingly, the protective cover of Perry is not formed integrally with the needle tip, requiring manual positioning which can be dangerous when attempting to thread a sharp needle into its protective casing. Further, careless or lazy users would be able to not use the protective casing, thereby lessening the overall safety effectiveness of the assembly. As a result, it would be highly beneficial to have a disposable needle head assembly which comes protectively encased so as to make it safe to attach to the syringe body, enables the needle tip to be visible and exposed prior to injection, thereby enabling a more accurate injection, and automatically becomes engaged in a protective orientation as a result of the normal use of the needle, that normal use including drawing medication from a vial as well as injecting a patient. The device of the present invention is designed specifically to meet these pressing needs for a needle whose tip will be exposed only when purposefully required and will minimize accidents due to carelessness by ensuring that the needle is protected automatically and not as a result of affirmative steps taken by a user.

SUMMARY OF THE INVENTION

The present invention is directed towards a disposable needle head assembly to be used with a standard syringe body. The assembly includes primarily a needle portion and a cover portion, with a hub of the needle portion being adapted for secure positioning on the syringe body. The hub of the needle portion has a generally uniform diametered, cylindrical exterior and a tapered axial opening therein. The axial opening extends from a narrow needle holding end from which the hypodermic needle protrudes, to an oppositely disposed, generally wide proximal attachment end which is secured to the syringe body by fastening means. Disposed about the needle portion is the cover portion which is generally cylindrical in shape and includes a distal face, a surrounding side wall structure, and an open proximal end. The cover portion has an inner diameter which is slightly larger than the outer diameter of the hub of the needle portion so as to provide a relatively tight fit, yet allow sliding movement of the cover portion axially over the needle portion. The needle portion passes into the cover portion through the open proximal end, and the needle tip protrudes from the cover portion through a central access opening formed in the distal face of the cover portion. Included to regulate the sliding movement of the cover portion over the needle portion are guide means. The guide means cause the cover portion to be positioned in either a retracted needle exposing position or an extended needle containing position, depending upon the requirements of the particular stage of use. The guide means include at least one recessed track disposed on the exterior of the hub. Correspondingly disposed on a interior of the surrounding side wall structure of the cover portion is an inwardly protruding nub which is adapted to be slidably fitted within the recessed track. The nub's engagement within the track secures the cover portion about the needle portion and regulates the movement of the cover portion in accordance with the movement of the nub within the track. Numerous engagement positions are included on the track, at least one of which is a needle exposing position which disposes the cover portion such that the needle tip protrudes through the central access opening in the cover portion, and such that the cover portion is retractable towards the hub upon injection of the hypodermic needle into an injecting surface and the contacting of the distal face of the cover portion with the injecting surface. Additionally, the track includes a needle containing position which is automatically entered into after the needle is removed from use on an individual. The needle containing position disposes the cover portion such that it substantially extends over the hypodermic needle and completely contains it therein. In order to facilitate the automatic return of the cover portion towards the needle tip, biasing means are positioned between the cover portion and the needle portion. The biasing means exert an axially outward, biasing force on the cover portion and the needle portion, thereby causing the cover portion to return to its normal position after it retracts during an injection, and move to the extended needle containing position after removal of the needle from an individual. Once the nub is in the needle containing position, and accordingly the cover portion is in an extended needle containing position, lock means of the assembly maintain the nub securely in the needle containing position, thereby assuring that the cover portion will not retract even if pressure is put on its distal face. Finally, a closure cap to completely seal the hypodermic needle within the cover portion is included, the closure cap being adapted to be secured over the central access opening in a distal face of the cover portion before and after use.

It is an object of the present invention to provide a disposable needle head assembly which is completely contained before use, automatically becomes contained after use, and includes an exposed needle tip only when actually necessitated.

Still another object of the present invention is to provide a disposable needle head assembly which is useable on a standard syringe body and includes a protective covering formed therewith, thereby eliminating necessity for a user to manually employ a protective covering before, after, or during use, and assuring that the protective covering is always utilized.

Still another object of the present invention is to provide a disposable needle head assembly which is protectively contained during injection into a patient as well as during and after injection into a vial of medication.

BRIEF DESCRIPTION OF THE DRAWINGS

For a fuller understanding of the nature of the present invention, reference should be had to the following detailed description taken in connection with the accompanying drawings in which:

FIG. 5 is a cross-sectional view of a second embodiment of the disposable needle head assembly of the present invention.

FIG. 6 is an exploded, partial cutaway view of the second embodiment of the disposable needle head assembly of the present invention.

Like reference numerals refer to like parts throughout the several views of the drawings.

DETAILED DESCRIPTION OF THE PREFERRED EMBODIMENT

Figure 1:
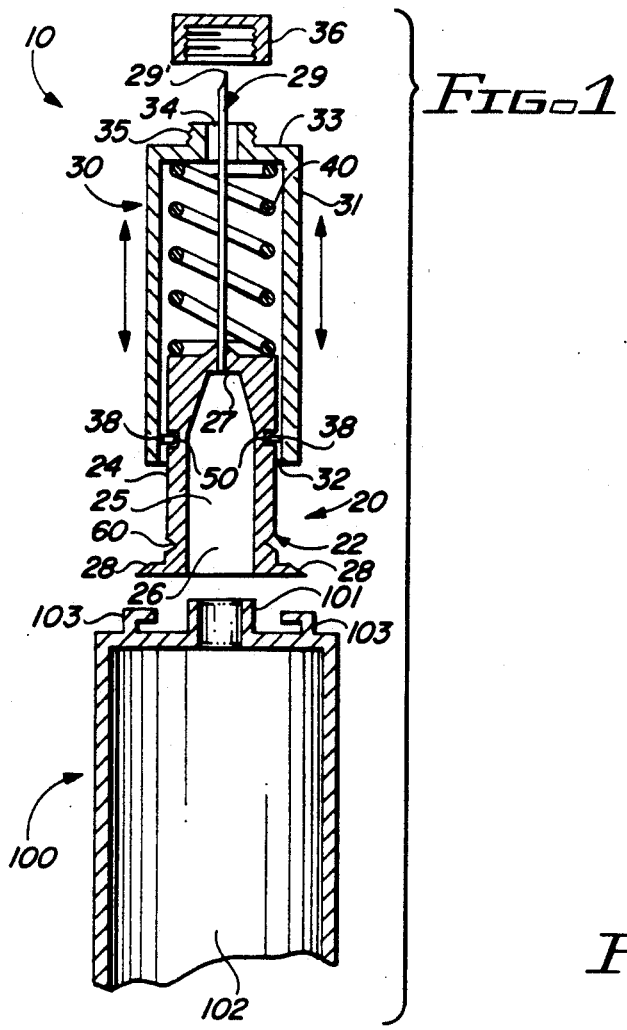
FIG. 1 is a cross-sectional view of a first embodiment of the disposable needle head assembly of the present invention.
Figure 2:
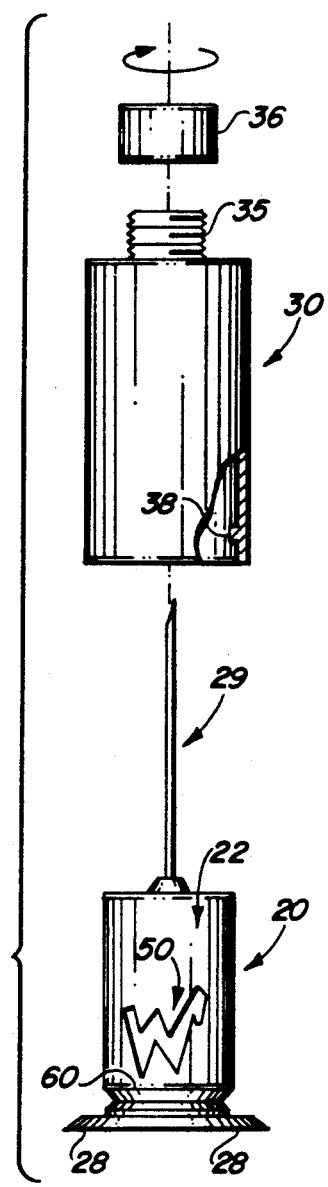
FIG. 2 is an exploded, partial cutaway view of the first embodiment of the disposable needle head assembly of the present invention.

Shown throughout FIGS. 1-6, the present invention is directed towards a disposable needle head assembly, generally indicated as 10. The assembly 10 is adapted to be fitted to a standard syringe body 100 in much the same manner as ordinary disposable needle assemblies, thereby enabling facilitated adaptation for use.

The needle head assembly 10 includes primarily a needle portion 20 and a cover portion 30 disposed thereon. The needle portion 20 includes a hub portion 22, which is adapted to be secured to the syringe body 100, and a hypodermic needle 29 extending from the hub portion. The hub portion 22 has a generally uniform diametered, cylindrical exterior 24, and a tapered axial opening 25 extending therethrough. The axial opening 25 includes a generally wide proximal attachment end 26 which is structured to be disposed over a collar portion 101 of the syringe body 100. Additionally, protruding outwardly from the hub portion 22 at this attachment end 26 are a pair of oppositely disposed, flange-type protrusions 28. The flange-type protrusions 28 are structured to be secured beneath a corresponding pair of lip segments 103 disposed on the syringe body 100, and accordingly, cause the hub portion 22 to form a tight seal with the syringe body 100, enabling an interior 102 of the syringe body 100 to be in fluid flow communication with the axial opening 25 in the hub portion 22. Oppositely disposed from the attachment end 26 is a narrow needle holding end 27. The axial opening 25 includes a narrowing taper leading to the needle holding end 27, thereby facilitating the fluid flow through the hub portion 22 from the interior 102 of the syringe body 100 to a hypodermic needle 29 which is securely disposed and held in the needle holding end 27.

Disposed over the needle portion 20 is the cover portion 30. The cover portion 30 includes a surrounding side wall structure 31, an open proximal end 32, and a distal face 33. An interior diameter defined between the side wall structure 31 of the cover portion 30 is adapted to be slightly larger than a diameter of the exterior 24 of the hub portion 22, thereby allowing sliding movement of the cover portion 30 over the hub portion 22. The needle portion 20 is disposed within the cover portion 30 through the open proximal face 32 thereof, and the distal face 33 of the cover portion includes a central access opening 34 to allow solely the hypodermic needle 29 to protrude therethrough.

Included as part of the disposable needle head assembly 10 so as to regulate the movement and disposition of the cover portion 30 over the needle portion 20, and more particularly over the hypodermic needle 29 and its sharp tip 29', are guide means. The guide means are adapted to control the disposition of the cover portion 30 between a retracted needle exposing position, in which the needle tip 29' protrudes from the cover portion 30, and an extended needle containing position wherein a distal face 33 of the cover portion 30 achieves maximum spacing from the hub portion 22 of the needle portion 20, thereby shielding the needle tip 29' completely within the cover portion 30. Shown in FIGS. 1 and 2, and FIGS. 5 and 6, the present invention includes two embodiments of the guide means, both of which utilize a guide track 50 and a protruding nub 38. Shown in FIGS. 1 and 2, the guide track 50 is carved in the exterior 24 of the hub portion 22, such that the nub 38 which protrudes inwardly from the surrounding side wall structure 31 of the cover portion 30 is disposed therein. Alternatively, as shown in FIGS. 5 and 6, a second embodiment of the assembly 10' includes the guide track 50 disposed in the surrounding side wall structure 31 of the cover portion 30 and has the protruding nub 38 extending from the exterior 24 of the hub portion 22, through the track 50. Accordingly, by interlocking the nub 38 with the guide track 50, as is the case in both embodiments, the cover portion 30 is secured about the needle portion 2 such that it may not easily pop off, and the movement and disposition of the cover portion 30 about the needle portion 2 is directly controlled by the positioning of the nub 38 within the track 50. In the preferred embodiment, there are a plurality of the nubs 38 and tracks 50 disposed about the periphery of the hub portion 22 and cover portion 30 so as to provide a stable and secure fit.

Figure 4:
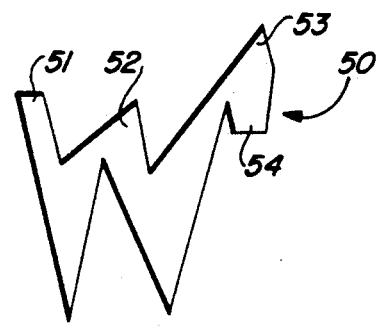
FIG. 4 is a closeup view of the track configuration used in the disposable needle head assembly of the present invention.

Turning to FIG. 4, in the preferred embodiment, the guide track 50 includes a generally W-type shape having a plurality of stop positions 51, 52, and 53 disposed therein. In order to assure that the nub 38 is always positioned within one of the stop positions 51, 52, or 53, biasing means 40 are disposed between the distal face 33 of the cover portion 30 and the hub portion 22 of the needle portion 20. The biasing means, which are preferably in the form of a coil spring 40 urge an outwardly biasing force on the cover portion 30 which pushes apart the cover portion 30 and the needle portion 20 to a spaced distance defined by the position of the protruding nub 38 within one of the stop positions 51, 52, or 53. Of the stop positions, at least one is a needle exposing position. In the preferred embodiment, there are two needle exposing positions 51 and 52. These needle exposing positions 51 and 52 position the cover portion 30 such that the needle tip 29' protrudes through the access opening 34 in the distal face 33 of the cover portion 30 making the needle tip 29' visible and enabling accurate injecting. In use, the needle tip 29' is positioned at the site of injection, as is normal procedure, and is injected. Upon injection of the hypodermic needle 29 into either an individual or a vial of medication or the like, the distal face 33 of the cover portion 30 contacts the injected surface which accordingly exerts an inward force on the cover portion 30 causing the spring 40 to compress and exposing a greater quantity of the needle 29. With relation to the guide track 50, as the retracting force is exerted on the cover portion 30, the nub 38 moves from an initial stop position 51 until the force is removed. Upon removal of the force, the spring 40 increases the spacing between the nub portion 22 and the distal face 33 of the cover portion 30 resulting in the protruding nub 38 rising to a next one of the stop positions 52 as a result of the angled configuration of the guide track 50. In the preferred embodiment, both stop positions 51 and 52 are needle exposing positions because during normal use, two injections are usually necessary, one into a vial either to draw or insert a fluid dose or sample and a second into a patient. After administering an injection during which the protruding nub 38 was in a final one of the stop positions 52, release of the retracting force on the cover portion 30 results in the nub 38 rising into a needle containing position 53 in the track 50. The needle containing position 53 is defined by the cover portion 30 being extended to a point where the entire needle 29, and most importantly the needle tip 29' is shielded completely within the cover portion 30. Additionally, in order to prevent accidental retraction of the cover portion 30 if a retracting force is exerted thereon, lock means 54 in the form on a shortened nub containing wall 54 is provided in guide track 50. The containing wall 54 is disposed such that the nub 38 may not move beyond the wall 54 once in the needle containing portion, thereby preventing the cover portion 30 from retracting and exposing the needle tip 29'.

Figure 3:
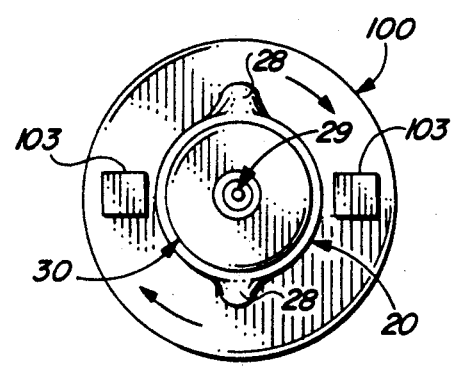
FIG. 3 is a top view of the disposable needle head assembly atop a standard syringe body.

In order to assure further safety in the use of the needle assembly 10, a closure cap 36 is specifically structured to be secured over the access opening 34 in the distal face 33 of the cover portion 30. The access opening 34 includes a protruding lip 35 upon which the closure cap 36 is screwed. Referring to FIG. 3, the needle assembly 10 is secured to the syringe body by rotating the needle assembly 10 clockwise until the protruding flange portions 28 slide underneath the lip portions 103 of the syringe 100. In order to assure that this secure engagement of the flange portions 28 beneath the lip portions 103 of the syringe body 100 is maintained when the closure cap 38 is removed from the cover portion 30, the threading on the interior of the closure cap 36 and the exterior of the protruding lip 35 on the cover portion 30 are reverse oriented such that clockwise rotation removes the closure cap 36, further tightening the engagement of the flange portions 28 beneath the lip portions 103 of the syringe body 100.

Immediately after removal of the needle from a patient, the closure cap 36 should be secured to access opening 34. At this time, the needle and end cover portion 30 can be removed from the syringe and properly disposed of in accordance with accepted medical waste disposal procedures. To facilitate removal of the needle 29 and cover portion 30 from the syringe, an annular groove 60 is provided about the external surface of the hub portion 22, defining a ring of reduced thickness thereabout. By grasping the cover portion 30 and applying a bending or shearing force perpendicular to the longitudinal axis of the syringe, the hub will be caused to break along the annular groove effectively separating the needle holding end 27, along with the needle 29 and cover portion 30, from the attachment end 26 which remains secured to the syringe 100.

While the instant invention has been shown and described in which are considered to be practical and preferred embodiments, it is recognized that departures may be made therefrom within the scope of the claims as set forth herein which are to be accorded the full scope and spirit of this invention and are not to be limited except within the doctrine of equivalents.

Now that the invention has been described,

What is claimed is:

1. To be used with a standard syringe body, a disposable needle head assembly comprising:
   a needle portion and a cover portion, said needle portion including an attachment hub and a hypodermic needle,
   said hub having a generally uniform diametered cylindrical exterior and a tapered axial opening extending therethrough,
   said tapered axial opening including a narrow needle holding end structured and disposed to securely hold the hypodermic needle therein in fluid flow communication with said axial opening, and a generally wide proximal attachment end structured and disposed to securely mount said hub to the syringe body such that an interior of the syringe body is in fluid flow communication with said axial opening in said hub,
   fastening means structured and disposed to lockingly secure said hub to the syringe body,
   said cover portion being generally cylindrical in shape and including a distal face, a surrounding side wall structure, an interior, and an open proximal end in fluid communication with said interior,
   an inner diameter of said cover portion within said interior being slightly larger than an exterior diameter of said hub so as to allow slidable receipt and containment of said needle portion into said cover portion through said open proximal end thereof,
   said distal face of said cover portion including a central access opening structured and disposed to allow passage of said hypodermic needle therethrough, guide means structured and disposed to regulate movement of said cover portion about said needle portion between a retracted, needle exposing position and an extended, needle containing position, said guide means including at least one guide track and at least one protruding nub extending into said slidable along said track, and maintaining said cover portion secured about said needle portion while regulating the movement of said cover portion relative to said needle portion, said track including a plurality of stop positions, biasing means positioned between said cover portion and said needle portion and being structured and disposed to exert an axially outward, biasing force on said cover portion away from said needle portion causing said nub to slidably move to one of said stop positions in said track, said stop positions of said track including at least one needle exposing position structured and disposed to cause said cover portion to be positioned about said needle portion such that said needle protrudes through said central access opening in said distal face of said cover portion, said stop positions of said track further including a needle containing position structured and disposed to cause said cover portion to be positioned in said extended, needle containing position wherein said hypodermic needle is completely shielded within said interior of said cover portion, lock means in said needle containing position of said track, said lock means being structured and disposed to maintain said nub securely positioned in said needle containing position, thereby preventing accidental retraction of said cover portion and exposure of said needle, a closure cap structured and disposed for sealed positioning over said central access opening in said distal face of said cover portion, and said guide means being structured to cause said nub to exit a first stop position upon exertion of an initial external force on said distal face of said cover portion resulting in said cover portion retracting, and upon release of said externally exerted force, said nub being caused to move to a next succeeding stop position in said track.

2. An assembly as recited in claim 1 wherein said fastening means includes a pair of oppositely disposed, flange type protrusions extending outwardly from said proximal attachment end of said hub and being structured and disposed for locking receipt under a pair of corresponding lip segments on the syringe body.

3. An assembly as recited in claim 2 wherein said central access opening on said distal face of said cover portion includes an outwardly protruding, externally threaded lip structured and disposed for receipt of said closure cap thereon, said closure cap being internally threaded.

4. An assembly as recited in claim 3 wherein said external threading of said lip of said central access opening and said internal threading of said closure cap are reverse threaded such that clockwise rotation of the assembly so as to lock said hub onto said syringe body results in unscrewing of said closure cap from said cover portion.

5. An assembly as recited in claim 1 wherein there are two of said needle exposing positions in said track.

6. An assembly as recited in claim 5 wherein there are two oppositely disposed, recessed tracks.

7. An assembly as recited in claim 5 wherein there are three spaced recessed tracks.

8. An assembly as recited in claim 1 wherein said guide track is disposed in said exterior of said hub of said needle portion.

9. An assembly as recited in claim 8 wherein said protruding nub extends inwardly from said surrounding side wall structure of said cover portion.

10. An assembly as recited in claim 1 wherein said guide track is disposed in said surrounding side wall structure of said cover portion.

11. An assembly as recited in claim 10 wherein said protruding nub extends outwardly from said exterior of said hub of said needle portion.

12. An assembly as recited in claim 1 wherein said hub included detachment means thereon to enable removal and subsequent disposal of said needle and said cover portion.

13. An assembly as recited in claim 12 wherein said detachment means includes a breakaway zone formed in said hub and being structured and disposed to facilitate separation of said hub, said needle and said cover portion from said syringe body.

14. An assembly as recited in claim 13 wherein said breakaway zone includes an annular groove formed about said cylindrical exterior of said hub defining a ring of reduced diameter thereabout.

15. To be used with a standard syringe body, a disposable needle head assembly comprising:

a needle portion and a cover portion, said needle portion including an attachment hub and a hypodermic needle, said hub having a generally uniform diametered cylindrical exterior and a tapered axial opening extending therethrough, said tapered axial opening including a narrow needle holding end structured and disposed to securely hold the hypodermic needle therein in fluid flow communication with said axial opening, and a generally wide proximal attachment end structured and disposed to securely mount said hub to the syringe body such that an interior of the syringe body is in fluid flow communication with said axial opening in said hub, fastening means structured and disposed to lockingly secure said hub to the syringe body, said cover portion being generally cylindrical in shape and including a distal face, a surrounding side wall structure, an interior, and an open proximal end in fluid communication with said interior, an inner diameter of said cover portion within said interior being slightly larger than an exterior diameter of said hub so as to allow slidable receipt and containment of said needle portion into said cover portion through said open proximal end thereof, said distal face of said cover portion including a central access opening structured and disposed to allow passage of said hypodermic needle therethrough, guide means structured and disposed to regulate movement of said cover portion about said needle portion between a retracted, needle exposing position and an extended, needle containing position, said guide means including at least one guide track and at least one protruding nub extending into said slidable along said track, and maintaining said cover portion secured about said needle portion while regulating the movement of said cover portion relative to said needle portion, said track including a plurality of stop positions, biasing means positioned between said cover portion and said needle portion and being structured and disposed to exert an axially outward, biasing force on said cover portion away from said needle portion causing said nub to slidably move to one of said stop positions in said track, said stop positions of said track including at least one needle exposing position structured and disposed to cause said cover portion to be positioned about said needle portion such that said needle protrudes through said central access opening in said distal face of said cover portion, said stop positions of said track further including a needle containing position structured and disposed to cause said cover portion to be positioned in said extended, needle containing position wherein said hypodermic needle is completely shielded within said interior of said cover portion, lock means in said needle containing position of said track, said lock means being structured and disposed to maintain said nub securely positioned in said needle containing position, thereby preventing accidental retraction of said cover portion and exposure of said needle, a closure cap structured and disposed for sealed positioning over said central access opening in said distal face of said cover portion, said guide means being structured to cause said nub to exit a first stop position upon exertion of an initial external force on said distal face of said cover portion resulting in said cover portion retracting, and upon release of said externally exerted force, said nub being caused to move to a next succeeding stop position in said track, and detachment means on said hub to enable removal and subsequent disposal of said needle and said cover portion and including a breakaway zone formed in said hub and being structured and disposed to facilitate separation of said hub, said needle and said cover portion from said syringe body, said breakaway zone including an annular groove formed about said cylindrical exterior of said hub defining a ring of reduced diameter thereabout.

* * * * *